United States Patent [19]

Cipollina et al.

[11] Patent Number: 4,956,368
[45] Date of Patent: Sep. 11, 1990

[54] METABOLITES AND PRODRUG FORMULATIONS OF 8-[4-[4-(1,2-BENZISOTHIAZOL-3-YL)-1-PIPERAZINYL]BUTYL]-8-AZASPIRO[4.5]-DECANE-7,9-DIONE

[75] Inventors: Joseph A. Cipollina, Middletown, Conn.; Edward H. Ruediger, Greenfield Park, Canada

[73] Assignee: Bristol-Myers Company, New York, N.Y.

[21] Appl. No.: 383,475

[22] Filed: Jul. 24, 1989

[51] Int. Cl.⁵ .................. A61K 31/495; C07D 401/14
[52] U.S. Cl. .................................... 514/254; 544/230; 544/368
[58] Field of Search .................. 544/230, 368; 514/254

[56] References Cited

U.S. PATENT DOCUMENTS

| | | | |
|---|---|---|---|
| 4,104,388 | 8/1978 | Wade et al. | 514/254 |
| 4,411,901 | 10/1983 | Temple, Jr. et al. | 424/250 |
| 4,590,196 | 5/1986 | Smith et al. | 514/253 |
| 4,656,173 | 4/1987 | Yevich et al. | 514/253 |
| 4,677,104 | 6/1987 | New et al. | 514/222 |
| 4,757,073 | 7/1988 | New et al. | 514/252 |

FOREIGN PATENT DOCUMENTS 0196096 10/1986 European Pat. Off. .

OTHER PUBLICATIONS

White et al., Chem. Abst. 105-183821x (1986).
Aguirre, Chem. Abst. 108-6045p (1988).
Hyslop et al., Chem. Abst. 111-33479b (1989).
Strupczonski, Chem. Abst. 103-123473j (1985).
Kennis et al., Chem. Abst. 106-67292x (1987).
Lowe et al., Chem. Abst. 110-39024a (1989).
Janssens et al., Chem. Abst. 110-212855x (1989).
Yamawaki and Ando, "Potassium Fluoride on Inorganic Solid Supports . . .", *Chemistry Letters,* pp. 755-758 (1979).
Gore and Vederas, "Oxidation of Enolates by Dibenzyl Peroxydicarbonate to Carbonates of a-Hydroxy . . .", *J. Org. Chem.,* pp. 3700-3704, vol. 51, No. 19 (1986).
Depres and Greene, "Improved Selectivity in the Preparation of Some 1,1-Difunctionalized 3-Cyclopentenes . . .", *J. Org. Chem.,* pp. 928-931, vol. 49, No. 5 (1984).

*Primary Examiner*—Cecilia Shen
*Attorney, Agent, or Firm*—Richard P. Ryan; William T. Han

[57] ABSTRACT

Various metabolites and prodrug formulations of 8-[4-[4-(1,2-benzisothiazol-3-yl)-1-piperazinyl]butyl]-8-azaspiro[4.5]decane-7,9-dione which are particularly useful in the treatment of psychotic disorders, especially derivatives thereof which have been oxygenated at specified sites about the original structure, rearranged compounds, and prodrug formulations of these species. One particularly desired group of compounds have the general Formula I where

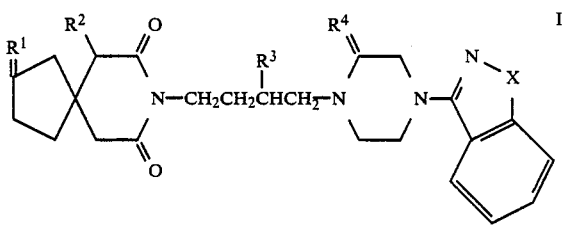

$R^1$ is hydrogen, hydroxyl, alkoxy, acyloxy and oxo;
$R^2$ is hydrogen, methyl, hydroxyl, alkoxy, and acyloxy;
$R^3$ is hydrogen, hydroxyl, and methoxy:
$R^4$ is hydrogen, methyl and oxo; and
X is S, SO, and $SO_2$.

21 Claims, No Drawings

METABOLITES AND PRODRUG FORMULATIONS OF 8-[4-[4-(1,2-BENZISOTHIAZOL-3-YL)-1-PIPERAZINYL]BUTYL]-8-AZASPIRO[4.5]DECANE-7,9-DIONE

BACKGROUND OF THE INVENTION

The present invention provides numerous novel metabolites and prodrug formulations of 8-[4-[4-(1,2-benzisothiazol-3-yl)-1-piperazinyl]butyl]-8-azaspiro[4.5]-decane-7,9-dione (tiospirone) which are particularly useful in the treatment of psychotic disorders. In particular, the present invention includes substituted derivatives of the title compound and methods for their preparation such that one preferred group of compounds have the general Formula (I);

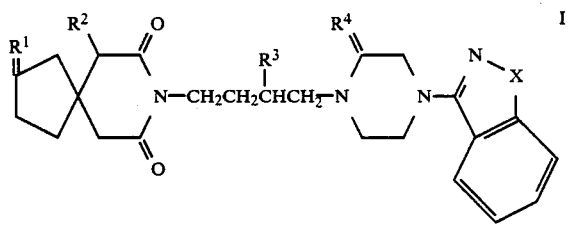

wherein $R^1$ is selected from the group consisting of hydrogen, hydroxyl, lower ($C_1$–$C_4$) alkoxy, higher ($C_9$–$C_{17}$) acyloxy and oxo;

$R^2$ is selected from hydrogen, methyl, hydroxyl, lower ($C_1$–$C_4$) alkoxy, higher ($C_9$–$C_{17}$) acyloxy and acetoxy;

$R^3$ is hydrogen, hydroxyl, and methoxy;

$R^4$ is hydrogen, methyl and oxo, with the proviso that $R^1$ and $R^2$ cannot be acyloxy simultaneously and the solid and dotted lines refer to either a double covalent bond or a single covalent bond with another hydrogen atom covalently bonded to the carbon terminus end;

X is selected from the group consisting of S, SO, and $SO_2$, with the proviso that X cannot be S or SO when $R^1$, $R^{2,}$ $R^3$ and $R^{4,}$ are all hydrogen; and the pharmaceutically acceptable salts and solvates thereof.

Tiospirone is an antipsychotic agent predicted to have low EPS liability. Tiospirone possesses potent in vitro interactions at the serotonin 5-$HT_{1A}$ and 5-$HT_2$ receptors as well as at the sigma and alpha -adrenergic receptor sites. It also demonstrates appreciable in vitro affinity for dopamine $D_2$ receptors (a standard test predictive of neuroleptic activity) but does not cause dopamine receptor supersensitivity following chronic administration.

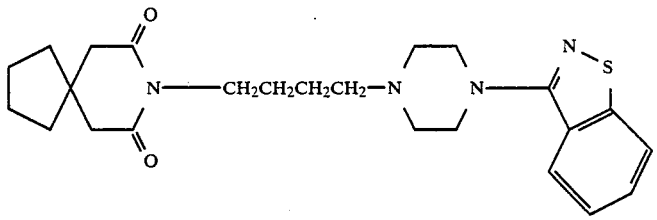

Specifically, tiospirone (i) is an azaspirodecanedione bridged by a tetramethylene chain to a benzisothiazolyl piperazine. Its chemical name is 8-[4-[4-(1,2-benzisothiazol-3-yl)-1-piperazinyl]butyl]-8azaspiro[4.5]decane-7,9-dione. Such heterocyclic carbon 4.5]decane-7,9-dione. Such heterocyclic carbon compounds having drug and bio-affecting properties are set forth in U.S. Pat. No. 4,411,901 (Temple, Jr. et al.), issued Oct. 25, 1983.

The Temple, et al., patent discloses N,N-disubstituted piperazinyl derivatives, wherein one substituent is benzisothiazol-3-yl or benzisoxazol-3-yl and the other is alkylene attached to heterocycles such as azaspiro[4.5]decanedione, dialkylglutarimide, thiazolidinedione and spirocyclopentylthiazolidinedione or butyrophenone-like groups. A preferred compound having antipsychotic activity is 8-[4-[4-(1,2-benzisothiazol-3-yl)-1-piperazinyl]butyl]-8-azaspiro[4.5]decane-7,9-dione, i.e. tiospirone (i).

The compounds disclosed in the I.emple, et al. patent are useful pharmacological agents with psychotropic properties. In this regard, they typically exhibit selective central nervous system (CNS) activity at nontoxic doses and are of particular interest as neuroleptic (antipsychotic) agents. As with other known antipsychotics, the tiospirone compound evokes certain responses in standard in vivo and in vitro pharmacological test systems which are known to correlate well with relief of anxiety and symptoms of acute and chronic psychosis in man.

Studies into the metabolism and pharmacokinetics (MAP) of tiospirone have identified novel oxygenated derivatives of the tiospirone molecule which possess biological activities similar to the parent molecule. One such oxygenated derivative of tiospirone is set forth in U.S. Pat. No. 4,656,173 (Yevich, et al.), issued Apr. 7, 1987. This oxygenated tiospirone compound (ii) has the general formula 8-[4-[4-(1-oxo-1,2-benzisothiazol-3-yl)-1-piperazinyl]butyl]-8-azaspiro[4.5]decane-7,9-dione.

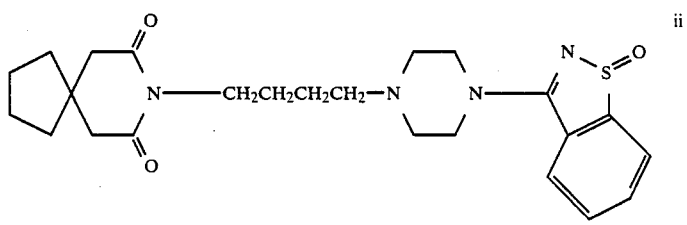

It is noteworthy that the attenuation of in vitro binding affinity observed for this compound compared to tiospirone did not affect its potency in in vivo screens predictive of antipsychotic activity (See Tables 6 and 7). Metabolic interconversion between the sulfur-oxide (ii) and tiospirone (i) has been proposed thus categorizing the sulfoxide as a prodrug form of the parent drug. This principle is further discussed in the Yevich, et al. patent, incorporated herein by reference.

The aforementioned MAP studies also identified metabolites where metabolic oxygenation occurred at various carbon atoms about the molecule. Metabolic rearrangement of the compound produced by hydroxylation at C-6 of the azaspirodecanedione portion of the molecule has been observed to produce an oxaspirononanone heterocycle. Therefore, the present invention also includes the rearranged metabolites of tiospirone such that a preferred group of compounds have the general Formula (II):

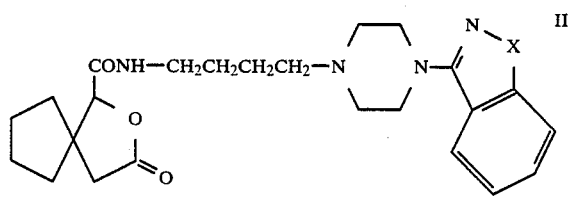

wherein X is selected from the group consisting of S, SO and SO$_2$; and pharmaceutically acceptable acid addition salts and solvates thereof.

Preparation of the aforementioned entities require the synthesis of necessary, novel precursors to the compounds of the present invention. Subsequently, the present invention also includes novel substituted derivatives of the benzisothiazole-piperazine moiety such that a preferred group of compounds have the general Formula (III):

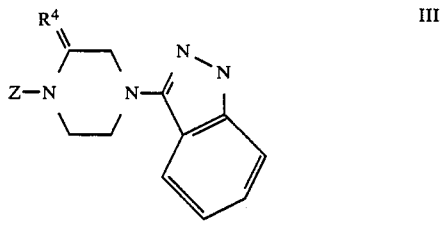

wherein R$^4$ is selected from the group consisting of hydrogen, methyl and oxo; X is selected from the group consisting of S, SO, and SO$_2$; and Z is either hydrogen or lower (C ) alkyloxycarbonyl, with the proviso that R$^4$ and Z cannot both be hydrogen when X is S or S0$_2$, and the solid and dotted lines refer to either a double covalent bond or a single covalent bond with another hydrogen atom covalently bonded to the carbon terminus end; and the pharmaceutically acceptable acid addition salts and solvates thereof.

Compounds related to those of Formula III having antiinflammatory properties are set forth in U.S. Pat. No. 4,104,388 (Wade, et al.) issued Aug. 1, 1978. The Wade, et al. patent discloses 3-substituted benzisothiazole 1,1-dioxides. While these antiinflammatory compounds are generally related to the compounds of the instant invention, they are nonetheless structurally distinguishable mainly on the basis of substitution about the 3-piperazinyl moiety.

While the prior art compounds listed above are generally related to the compounds of the instant invention, they are nonetheless distinguishable thereof structurally on the basis that the compounds of the instant invention are (1) oxygenated at designated sites about the compound, (2) rearranged compounds, and/or (3) novel precursors of the aforementioned compounds. None of the aforementioned references disclose or suggest the specific metabolites or rearranged metabolites of the antipsychotic agent tiospirone as set forth in the present invention. Furthermore, additional advantages of the present invention shall become apparent as described below.

SUMMARY AND DETAILED DESCRIPTION OF THE INVENTION

The present invention provides numerous novel metabolites and prodrug formulations of tiospirone as set forth below.

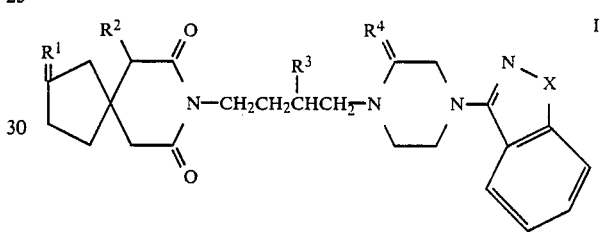

wherein R$^1$ is selected from the group consisting of hydrogen, hydroxYl, lower (C$_1$-C$_4$) alkoxy, higher (C$_9$-C$_{17}$) acyloxy and oxo;

R$^2$ is selected from hydrogen, methyl, hydroxyl, lower (C$_1$-C$_4$) alkoxy, higher (C$_9$-C$_{17}$) acyloxy and acetoxy;

R$^3$ is hydrogen, hydroxyl, and methoxy:

R$^4$ is hydrogen, methyl and oxo, with the proviso that R$^1$ and R$^2$ cannot be acyloxy simultaneously and the solid and dotted lines refer to either a double covalent bond or a single covalent bond with another hydrogen atom covalently bonded to the carbon terminus end;

X is selected from the group consisting of S, SO, and SO$_2$, with the proviso that X cannot be S or SO when R$^1$, R$^2$, R$^3$ and R$^4$ are all hydrogen; and the pharmaceutically acceptable salts and solvates thereof.

A compound of Formula II

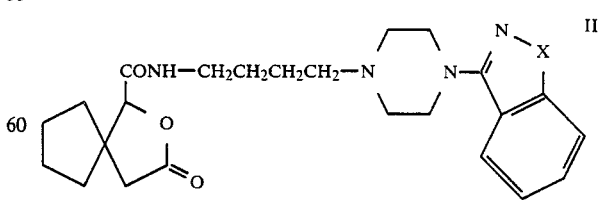

wherein X is selected from the group consisting of S, SO and SO$_2$; and pharmaceutically acceptable acid addition salts and solvates thereof.

A compound of Formula III

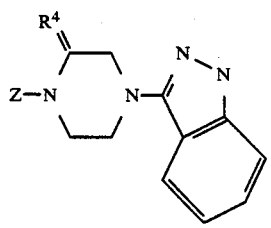

III wherein R[4] is selected from the group consisting of hydrogen, methyl and oxo; X is selected from the group consisting of S, SO, and $SO_2$; and Z is either hydrogen or lower ($C_1$-$C_4$) alkyloxycarbonyl, with the proviso that R[4] and cannot both be hydrogen when X is S or $SO_2$, and the solid and dotted lines refer to either a double covalent bond or a single covalent bond with another hydrogen atom covalently bonded to the carbon terminus end; and the pharmaceutically acceptable acid addition salts and solvates thereof.

The pharmaceutically acceptable acid addition salts of the invention are those in which the anion does not contribute significantly to the toxicity or pharmacological activity of the salt and, as such, they are the pharmacological equivalents of the bases of Formulas I, II and III compounds, respectively. The salts are routinely made by admixture of a Formula I, II, or III base with a selected acid, preferably by contacting solutions employing an excess of commonly used inert solvents such as ether, benzene, ethanol, ethyl acetate, acetonitrile, and water. The salt form may also be prepared by any of the other standard methods detailed in the literature and available to any practitioner skilled in the art.

It is a further object of the present invention to provide a process for ameliorating a psychotic state in a mammal in need of such treatment which comprises systemic administration to the mammal an effective antipsychotic dose of any of the compounds of Formulas I, II and III.

The administration and dosage regimen of compounds of Formulas I, II, and III, is considered to be done in the same manner as for the reference compound clozapine, of The Merck Index, 10th Edition, (1983), page 344, and references therein. Although the dosage and dosage regimen must in each case be carefully adjusted, utilizing sound professional judgement and considering the age, weight and condition of the recipient, the route of administration and the nature and gravity of the illness, generally the daily dose will be from about 0.05 to about 20 mg/kg, preferably, about 0.1 to about 5 mg/kg when administered parenterally, and larger doses when orally administered. In some instances, a sufficient therapeutic effect can be obtained at lower doses while in others, larger doses will be required.

Therapeutically, the instant compounds are generally given as pharmaceutical compositions comprised of an effective antipsychotic amount of a compound of either Formula I, II, or III, or a pharmaceutically acceptable acid addition salt thereof, and a pharmaceutically acceptable carrier, optionally with pharmaceutically acceptable adjuvants and excipients employing conventional techniques. Pharmaceutical compositions for effecting such treatment will contain a major or minor amount, e.g., from 95 to .05% of at least one compound of the present invention in combination with a pharmaceutical carrier, the carrier comprising one or more solids, semi-solids, or liquid diluent, filler, and formulation adjuvant which is non-toxic, inert and pharmaceutically acceptable. See U.S. Pat. No. 4,677,104 (New, et al.), issued June 30, 1987, which is incorporated herein by reference.

As indication of the psychotropic activity and specificity of a compound, state of the art in vitro central nervous system receptor binding (RB) methodology can be employed. Certain compounds (commonly referred to as ligands) have been identified which preferentially bind to specific high affinity sites in brain tissue dealing with psychotropic activity. Inhibition of radiolabeled ligand binding at such sites is considered a measure of the test compound's ability to affect corresponding central nervous system function in vivo.

Some of the more common binding tests employed are listed below in Table 1.

TABLE 1

| Receptor Binding (RB) Tests | | | |
|---|---|---|---|
| Test No. | Putative Receptor Site | Ligand Used | Specific Binding Agent |
| RB1 | Dopamine/Spiperone/ neuroleptic | [$^3$H] Spiperone | D(+)Butaclamol |
| RB2 | Alpha-1 | [$^3$H] WB-4104 | Phentolamine |
| RB3 | Serotonin Type 2 (5-$HT_2$) | [$^3$H] Spiperone | D-Lysergide |
| RB4 | Serotonin Type 1A (5-$HT_{1A}$) | [$^3$H] 8-OH-DPAT | 8-OH-DPAT |

References:
RB1 - Burt, et al., Molecular Pharmacology, 12, 800 (1976); Science, 196, 326 (1977); Crease, et al., Science, 192, 481 (1976).
RB2 - Crews, et al., Science, 202, 322 (1978); Rosenblatt, et al., Brain Res., 160, 186 (1979); U'Pritchard, et al., Science, 199, 197 (1978); Molec. Pharmacol. 13, 454 (1977).
RB3 - Peroutka and Snyder, Molec. Pharmacol., 16, 687 (1979).
RB4 - Peroutka, Brain Res., 344, 167 (1985).

Data derived from the above binding tests demonstrate that the compounds of the instant invention have modest to low affinity for dopaminergic receptors and significantly high affinities for both serotonin type 1A and type 2 receptor sites (Table 6). The lack of dopaminergic binding affinities demonstrated by the subject compounds is believed to relate to a reduced liability toward induction of undesirable extrapyramidal side effects common to most currently used antipsychotic agents.

Binding activity at the alpha-1 receptor indicates that the compounds will probably possess a sedating component of activity which is often desirable in the treatment of subgroups of psychotic patients.

The following in vivo test systems (Table 2) are illustrative of the conventional testing used to classify and differentiate a psychotropic agent from a non-specific CNS depressant.

TABLE 2

1. Conditioned Avoidance Response (CAR) - measure of a drug's tranquilizing activity as determined by its' attenuation of avoidance response to electrical shock in trained fasted rats. cf: Albert, Pharmacologist, 4, 152 (1962); Wu et al., J. Med. Chem., 12, 876–881 (1969).
2. Inhibition of Apomorphine-Induced (APO) Stereotypy - an assessment of blockade of dopaminergic activity in rats as measured by attenuation of the behavioral syndrome caused by the dopamine agonist, apomorphine. cf: Janssen, et al, Arzneimittel. Forsch., 17, 841 (1966).

According to the pharmacological profile established by these in vivo tests, the instant compounds have promising antipsychotic potential in that they are relatively potent in the CAR test, having oral $ED_{50}$ values less than 100 mg/kg body weight, and they effectively block apomorphine-induced stereotypy (Table 7). This blockade may reflect dopamine antagonist activity and is accepted as a fairly specific screen for neuroleptic activity.

In summary of the foregoing discussion, the present inventors have discovered that authentic metabolites as well as synthesized putative metabolites of tiospirone result in the production of novel antipsychotic compounds with in vitro activity tantamount to tiospirone and varying degrees of in vivo activity (See Tables 6 and 7).

Furthermore, enhancement of in vivo effects have been achieved through prodrug formulations of the authentic metabolites. That is, the metabolites, as such, being prone to glucuronidation and excretion have inherently reduced in vivo activity. Subsequently, attempts to increase their bioavailability through prodrug formulations have enabled observation of their in vivo effects. The novel compounds of the present invention are generally categorized as oxygenated derivatives of tiospirone, rearranged metabolites, or precursors thereof.

The compounds of the present invention are prepared by the general methodologies and unitary processes used in the synthesis of the parent drug, tiospirone. The methods are discussed at length in the previously cited U.S. patent of Temple, et. al., incorporated herein in entirety by reference. These methods may be adopted to variation in order to produce other compounds embraced by this invention but not specifically disclosed. Furthermore, variations of the methods to produce the same compounds in somewhat different fashion will also be evident to one skilled in the art. Certain examples will be given for specific illustration.

The compounds of Formula I may be prepared through oxidation of the appropriately substituted benzisothiazolepiperazine (BITP) precursor (Ia) as shown in Scheme I. Upon preparing a C-oxidized tiospirone metabolite of formula Ia using prior art and specific methods of the instant invention (vide infra), one may enact oxidation at the ring sulfur atom to afford the sulfoxide or sulfone derivative (Ib).

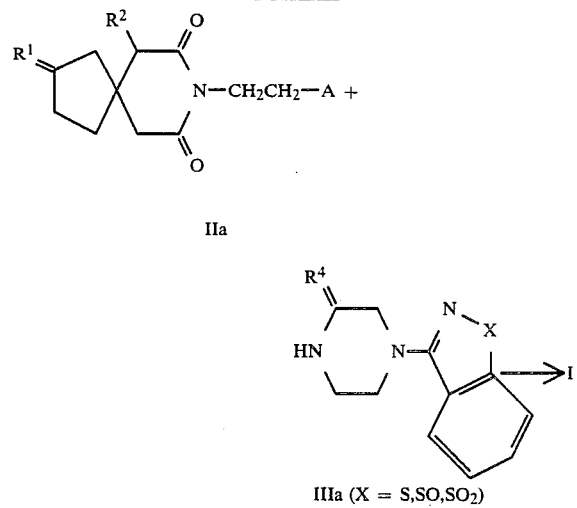

The nature of the group A is dependant upon the desired substituent for $R^3$ in the final product. The methods for preparing compounds containing the substitutions at R3 delineated in Formula I of the instant invention are contained in the literature and are evident to one skilled in the art. As an example, see European Patent Application 0196096 of Ishizumi, et al. published Oct. 1, 1986, incorporated herein in entirety by reference.

Similar to that shown in Scheme I, the compounds of Formula III may be prepared through oxidation of the appropriately substituted BITP precursor (IIIb) as shown in Scheme III. The preparation of compounds IIIb can be accomplished according to the prior art already cited or as described below.

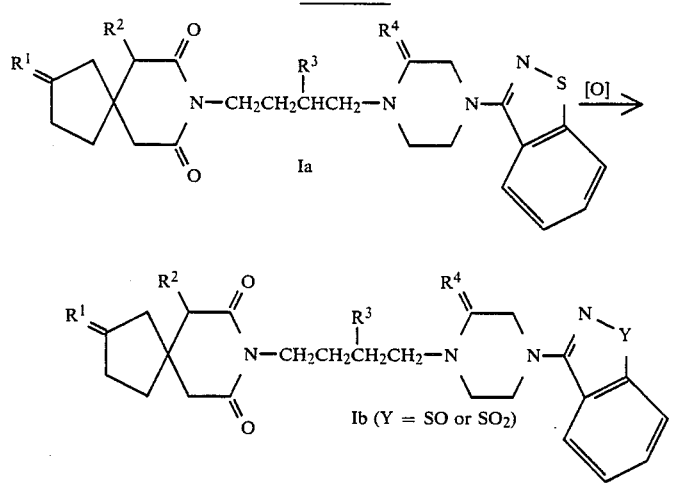

Alternatively, the compounds of Formula I may be prepared in a convergent manner through coupling of the compounds of Formula IIIa with the suitably selected antecedent (IIa) as shown in Scheme II.

Scheme III

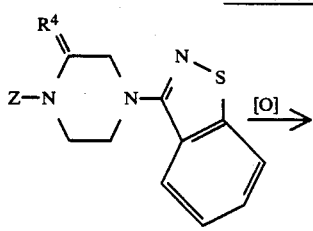

IIIb

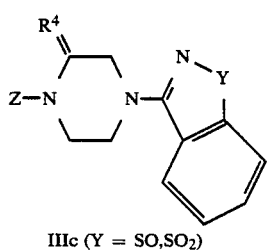

IIIc (Y = SO, SO$_2$)

Introduction of oxygen at the cyclopentyl region of the azaspirodecanedione moiety to produce $R^1$ substituents other than hydrogen could not be effected directly from the already intact system due to its remote locale. Subsequently, derivatization of this type was performed according to the general procedure shown in Scheme IV.

acetic anhydride for 15 h followed by in vacuo removal of the unreacted reagent. Preparation of the imide (IVg) (8-azaspiro[4.5]dec-2-ene-7, 9-dione) proceeded through an intermediary ring-opened carboxylate-amide (not isolated) from reaction of the anhydride with concentrated ammonium hydroxide. Closure to the desired imide was achieved in refluxing toluene with concomitant removal of water.

Hydroboronation-oxidation of the imide yielded the hydroxy-substituted imide (IVh) (2-hydroxy-8-azaspiro[4.5]decane-7,9-dione) in poor yield. Much better yields were obtained after N-alkylation to the tertiary imide (IVi). Standard hydroboronation-oxidation conditions typically resulted in isolation of the hydroxylated azaspirodecanedione (IVj) in 70 80% yield, depending on the nature of —R.

Pyridinium chlorochromate (PCC) oxidation of IVj in $CH_2C_{12}$ produced the keto-derivative IVk in high yields. Alternatively, derivatization of the hydroxyl group to the remaining R' substituents (IVl) of Formula I of the instant invention could be effected by admixture of IVj with an appropriate electrophile in an inert solvent. The reagents for effecting such a transition are readily available and voluminous in the literature and are obvious to one skilled in the art. Certain examples will be given for specific illustration.

Scheme V shows the general methodology utilized in preparing compounds where $R^2$ is other than hydrogen. Lithiation of Va with lithium hexamethyldisilazide (LHMDS) in anhydrous tetrahydrofuran (THF) and

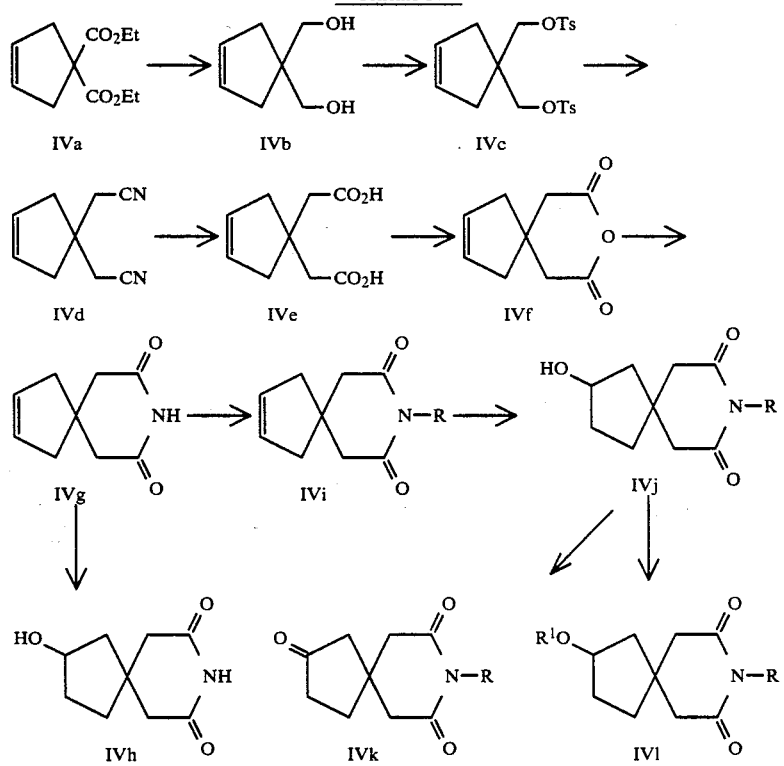

A four step chain homologation sequence was utilized to produce 3-cyclopentene-1,1-di-(methylcarboxylic acid) (IVe) from diethyl 3-cyclopentene-1,1-dicarboxylate (IVa) in an overall yield of 61%. Conversion to the anhydride (IVf) (8-oxaspiro[4.5]dec-2-ene-7,9-dione) was effected by refluxing the diacid in excess subsequent reaction of the anion with an appropriate electrophile resulted in substitution at the 6-position of the azaspirodecanedione moiety. Certain examples will be given for specific illustration.

When $R^2$ is hydroxyl, equilibrium controlled intramolecular rearrangement of Vb ($R^1$, $R^3$ and $R^4$ are all hydrogen), effected by potassium fluoride on alumina ($KF-Al_2O_3$) in acetonitrile yielded the lactone-amide (Vc) of Formula II in 89% converted yield.

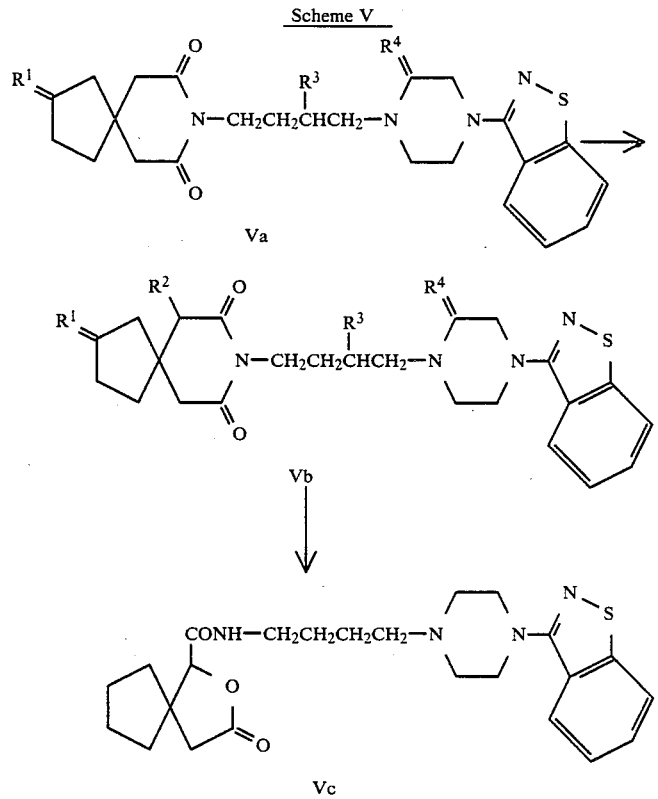

Scheme V

Compounds of Formula III where $R^4$ is oxo are prepared by tert-butoxycarbonyl (t-Boc) directed ruthenium tetroxide ($RuO_4$) oxidation as shown in Scheme VI. The t-Boc group is an efficient activator of the adjacent carbon atoms and facilitates α-oxidation in high yield. Methyl substitution for $R^4$ may be achieved by using the methyl-substituted piperazine derivative in the initial assembling of the molecule. This mode of substitution is elaborated further in the U.S. Pat. #4,590,196 of D. W. Smith, et al. issued May 20, 1986, incorporated herein in entirety by reference. These methods may be adapted to variation in order to produce other compounds embraced by this invention but not specifically disclosed. Furthermore, variations of the methods to produce the same compounds in somewhat different fashion will also be evident to one skilled in the art.

Scheme VI

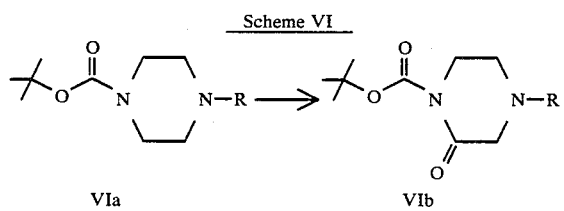

VIa     VIb

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope.

Melting points were taken in Kimax soft-glass capillary tubes using a Thomas-Hoover Uni-melt capillary melting point apparatus (Model 6406 K) and are uncorrected. Infrared spectra were recorded on either a Mattson Instruments, Inc. Alpha Centauri or a Perkin-Elmer 1800 Fourier Transform Infrared Spectrophotometer. Peak positions are given in reciprocal centimeters ($cm^{-1}$). NMR spectra were obtained on a Varian EM-360A (60 MHz $^1H$) or a Varian VXR-200 NMR spectrometer (200 MHZ $^1H$, 50 MHz $^{13}C$) equipped with a computer switchable 5.0 mm $^1H/^{13}C$ probe Chemical shifts are reported in parts per million (δ) downfield from tetramethylsilane. The deuterated NMR solvents contained 99.8–99.9% deuterium in the indicated positions and were obtained from MSD Isotopes, Montreal, Canada. 1H NMR coupling constants (J values) are listed in Hertz (Hz) and spin multiplicities are reported as singlet (s), doublet (d), triplet (t), quartet (q), multiplet (m), broad (b). CI mass spectral data were acquired on a Finnegan 4500 quadrupole mass spectrometer equipped with a Vacumetrics discharge chemical ionization probe using methane reagent gas at 0.3 torr source pressure. EI mass spectra were acquired on a Kratos Analytical MS25RFA equipped with an Ion Tech, LTD Xenon FAB source operated at 5 kV in either a glycerol or nitrobenzylalcohol (NOBA) matrix.

Microanalyses were performed by the Analytical Department of Bristol-Myers Company, Wallingford, CT. Analytical thin-layer chromatography (TLC) was performed on 0.25 mm EM silica gel 60 F-254 coated glass plates and preparative flash chromatography was performed on EM silica gel (32–62 μm). The solvent systems used are reported in each experimental. All solvents were Baker-Analyzed reagent grade and used without further purification except tetrahydrofuran (THF) which was distilled from sodium/benzophenone ketyl. n-Butyllithium was purchased from Alfa Ventron and titrated prior to use against diphenylacetic acid (used as titrant and indicator) in THF at room temperature. All non-aqueous reactions were carried out in flame-dried glassware under a nitrogen atmosphere.

GENERAL PROCEDURES FOR PREPARATION OF 1,2-BENZISOTHIAZOLE-1OXIDES FROM 1,2-BENZISOTHIAZOLES

Method A

The 1,2-benzisothiazole piperazine (BITP) derivative was dissolved in concentrated $H_2SO_4$ (7 mL/g BITP) and cooled to $-15°$ C. A 1:1 solution of concentrated $H_2SO_4$ and $HNO_3$ (2 mL/g BITP) was slowly added so that the internally monitored reaction temperature did not exceed $-5°$ C. Upon completion of addition, the reaction mixture was poured onto crushed ice (4× total volume) and stirred. The solution was maintained below 0° C. while being made basic with solid $Na_2CO_3$ The solution was repeatedly extracted with $CH_2Cl_2$ The extracts were combined, dried over anhydrous $Na_2SO_4$ and filtered. The solvent was evaporated in vacuo to yield the crude product which was further purified as required.

Method B

The 1,2-benzisothiazole piperazine (BITP) derivative was dissolved in $CH_2Cl_2$ (6 mL/mmol BITP) and cooled to $-78°$ C. A solution of meta-chloroperoxybenzoic acid (MCPBA) (80%, 1.1 equiv) in $CH_2Cl_2$ (3 mL/mmol) at $-78°$ C. was slowly added and the resultant mixture stirred for 0.5 h. The reaction was diluted with $CH_2Cl_2$, washed with $NaHCO_3$ and dried over anhydrous Na The dried organic phase was then filtered and evaporated in vacuo to afford the crude product which was further purified as required.

GENERAL PROCEDURE FOR THE PREPARATION OF 1,2-BENZISOTHIAZOLE-1,1-DIOXIDES FROM 1,2-BENZISOTHIAZOLES

Method C

The BITP derivative (1.0 equiv) was dissolved in $CH_2Cl_2$ (10 mL/g BITP) and added dropwise to a stirring 0.5 M solution of sodium metaperiodate ($NaIO_4$) (7.0 equiv) in 1:1 $H_2O$ methanol at room temperature. The reaction was stirred until TLC inspection indicated complete uptake of limiting reagent (typically 48h). The organic solvents were removed in vacuo and the resulting aqueous solution was made basic with 3N NaOH and extracted with $CH_2Cl_2$. The combined organic washings were dried ($Na_2SO_4$), filtered, and evaporated in vacuo, to afford the crude products which were further purified as required.

EXAMPLE 1

4-(1,2-Benzisothiazol-1-oxo-3-yl)-1H-piperazine (15)

This compound was prepared according to Method A (vide supra) from the art compound, 4-(1,2-benzisothiazol-3-yl)1H-piperazine (14). The crude reaction product was flash chromatographed with 15% MeOH/$CH_2Cl_2$ to afford a 50% yield of the title compound as a light yellow solid.

EXAMPLE 2

1,1-Dimethylethyl 4-(1,2-Benzisothiazol-1,1-dioxo-3-yl)-1piperazinecarboxylate (18)

This compound was prepared according to the general procedure given for the preparation of 1,2-benzisothiazole1,1-dioxides from 1,2-benzisothiazoles (Method C) starting from 1,1-dimethylethyl 4-(1,2-benzisothiazol-3-yl)-1piperazinecarboxylate. Recrystallization of the crude reaction product from ethanol afforded the title compound in 92% yield, mp 192–4° C.

EXAMPLE 3

8-[4-[4-(1,2-Benzisothiazol-1-oxo-3 yl)-1-piperazinyl]butyl]-6-hydroxy-8-azaspiro[4.5]decane-7,9-dione (11)

This compound was prepared according to Method B from 8-[4-[4-(1,2-benzisothiazol-3 yl)-1-piperazinyl]-butyl]-6-hydroxy-8-azaspiro[4.5]decane-7,9-dione (10). Flash chromatography of the crude reaction product in EtOAc/MeOH (7:3) afforded the title compound in 97% yield. Recrystallization from $CH_2Cl_2$/acetone gave a white, microcrystalline solid, mp 171–2° C.; IR (neat) 3380, 1722, 1672 $cm^{-1}$; $^1H$ NMR ($CDCl_3$) δ 7.88–7.80 (m, 2H), 7.52–7.32 (m, 2H), 4.27–4.14 (m, 2H), 4.12 (s, 1H) 3.90–3.79 (m, 4H), 3.5–3.41 (m, 2H), 3.29–3.17 (m, 4H), 2.85, 2.49 (AB q, J=17.4 Hz, 2H), 2.06–1.60 (br m, 11H), 1.38–1.18 (m, 2H): Anal. calcd for $C_{24}H_{32}N_4O_4S$/0.2 $H_2O$:
C, 60.53; H, 6.86; N, 11.77. Found: C, 60.51; H, 6.98; N, 11.58.

EXAMPLE 4

1,1-Dimethylethyl 4-(1,2-Benzisothiazol-3-yl)-1-piperazinecarboxylate

A solution of di-t-butyldicarbonate (22.06 g, 1.00 equiv) in 125 mL of $CH_2Cl_2$ was cooled to 0° C. BITP 14 (22.70 g, 1.02 equiv) in 50 mL of $CH_2Cl_2$ was slowly added via addition funnel: gas evolution was evident. The reaction was monitored by TLC while the solution was allowed to warm to room temperature. Upon completion of reaction (~3 h), the solvent was removed in vacuo and the resulting brown solid was recrystallized from $CH_3CN$ to afford the title compound (28.7 g, 2 crops, 89%) as a white solid, m.p. 105–7° C.; IR (KBr) 1700 $cm^{-1}$; $^1H$ NMR ($CDCl_3$) δ 7.88 (m, 2H), 7.42 (m, 2H), 3.66 (m, 4H), 3.49 (m, 4H), 1.49 (s, 9H); mass spectrum, m/z (relative intensity) 319 (M+, 35), 264 (100), 220 (31).

EXAMPLE 5

Preparation of Necessary Intermediate, 8-azaspiro[4.5]dec-2-ene-7,9-dione (IVg) from diethyl 3-cyclopentene-1,1-dicarboxylate (IVa) (Scheme IV)

Preparation of 1,1-Dihydroxymethyl-3-cyclopentene (IVb)

A mechanically-stirred suspension of lithium aluminum hydride (LAH) (23.0 g, 0.606 mol) in 800 mL of anhydrous THF was cooled to 0° C. Diester IVa (50.7 g, 0.239 mol) in 200 mL of anhydrous THF was slowly added via dropping funnel. Upon completion of addition, the mixture was allowed to stir at 0° C. for 4 h. The reaction was carefully quenched by sequential addition of 23 mL of H$_2$O, 23 mL of 3 N NaOH and 69 mL of H$_2$O. The reaction was filtered through a bed of Celite and the resultant cake was repeatedly washed with hot THF. Evaporation of the solvent in vacuo afforded an off-white solid which was recrystallized from toluene to yield 26.0 g (85%) of IVb as white needles, mp 168–70° C.; IR (KBr) 3320–3280, 3065, 2930, 2850, 1655, 1055, 1025 cm$^{-1}$; $^1$H NMR (CDCl$_3$) δ 5.53 (s, 2H), 3.62 (s, 4H), 2.15 (s, 4H); mass spectrum, m/z (relative intensity) 129 (M+1, 22), 111 (61), 93 (100).

Preparation of dimethyl 3-cyclopentene-1,1-di-(p-toluenesulfonate) (IVc)

Cyclopentene (IVb) (31.3 g, 0.245 mol) was dissolved in a minimal amount of pyridine (~90mL) and cooled to 0° C. p-Toluenesulfonyl chloride (141 g, 0.737 mol), dissolved in a minimum of pyridine (~200 mL), was added over the course of 2 h via a dropping funnel to the 0° C solution of IVb. After 5 h, the reaction mixture was poured onto 1 L of crushed ice and allowed to warm to room temperature. The resulting white solid was collected by filtration, washed with cold H$_2$O and allowed to air dry. Recrystallization from methanol yielded 98.0 g (92%) of IVc as white needles, mp 113–5° C.; IR (KBr) 1600, 1500, 1475, 1390, 1365, 1195, 1185 cm$^{-1}$; 1H NMR (CDCl$_3$) δ 7.72 (d, J=9.1 Hz, 4H), 7.30 (d, J=9.1 Hz, 4H), 5.47 (s, 2H), 3.87 (s, 4H), 2.45 (s, 6H), 2.13 (s, 4H); mass spectrum, m/z (relative intensity) 437 (M+1, 10), 265 (3), 173 (22), 155 (6), 93 (100).

Preparation of 1,1-di-(cyanomethyl)-3-cyclopentene (IVd)

A mechanically-stirred suspension of potassium cyanide (23.0 g, 0.353 mol) and potassium iodide (1.20 g, 7.23 mmol) in anhydrous dimethylformamide (DMF) (Aldrich Gold Label, 300 mL) was heated to 120° C. Ditosylate IVc (50.0 g, 0.115 mol) in anhydrous DMF (300 mL) was slowly added via dropping funnel. The reaction was followed by TLC until no starting material was evident (10–15 h). The reaction was allowed to cool to room temperature and then diluted with 1.8 L of H$_2$O. The solution was extracted repeatedly with 0.5 L portions of CH$_2$Cl$_2$. The organic extracts were combined and evaporated in vacuo to a brown liquid. Distillation under high vacuum afforded 15.8 g (94%) of IVd as a clear liquid, bp 118–21° C. at 1.0–1.2 mm; IR (neat) 3060, 2940, 2870, 2260, 1625, 1435, 1355 cm$^{-1}$; 1H NMR (CDCl$_3$) δ 5.61 (s, 2H), 2.60 (s, 4H), 2.42 (s, 4H); mass spectrum, m/z (relative intensity) 146 (M+ 21), 119 (4), 106 (100).

Preparation of 3-cyclopentene-1,1-di(methylcarboxylic acid) (IVe)

A mechanically-stirred solution of cyclopentene IVd (11.5 g, 78.6 mmol) in 200 mL of 70% EtOH/H$_2$O containing NaOH (35.0 g, 0.875 mol) was refluxed at 100° C. until a worked-up aliquot indicated the absence of starting material by TLC (1–2 days). The reaction was allowed to cool to room temperature and made strongly acidic with concentrated HCl. Any insoluble salts were filtered and washed with hot EtOH. Addition of H$_2$O at this point precipitated any amide intermediates from incomplete hydrolysis as brown solids. The solution was evaporated to dryness and the resultant solid was recrystallized from H$_2$O to yield 12.0 g (two crops, 83%) of IVe as white crystals, mp 134–6° C.; IR (KBr) 3110–3040, 2960–2920, 1730–1710, 1430, 1405 cm$^{-1}$; 1H NMR (DMSO-d6) δ 5.60 (s, 2H), 2.48 (s, 4H), 2.30 (s, 4H); mass spectrum, m/z (relative intensity) 185 (M+1, 72), 167 (100), 139 (8), 125 (21).

Preparation of 8-oxaspiro[4.5]dec-2-ene-7,9-dione (IVf)

Diacid IVe (10.5 g, 57.0 mmol) was dissolved in acetic anhydride (40.0 g, 0.392 mol) and heated to reflux for 15 h. The excess acetic anhydride was distilled off and the resulting oil taken up in a minimum of hot benzene. Slow dilution with hot hexane afforded 8.90 g (two crops, 95%) of IVf as off-white needles, mp 64–5° C.; IR (KBr) 1800, 1770, 1080, 1065, 955 cm$^{-1}$; 1H NMR (CDCl$_3$) δ 5.68 (s, 2H), 2.78 (s, 4H), 2.34 (s, 4H); mass spectrum, m/z (relative intensity) 167 (M+1, 100), 149 (15), 139 (8), 121 (8), 80 (10).

Preparation of 8-azaspiro[4.5]dec-2-ene-7,9-dione (IVg)

Anhydride IVf (8.78 g, 52.8 mmol) was carefully dissolved in concentrated ammonium hydroxide solution (25.0 g, 0.411 mol) and heated at 100° C. for 2 h. The reaction vessel was fitted with a dean-stark trap and the reaction volume was doubled with toluene. The solution was refluxed for 1–2 days until evolution of H$_2$O ceased. The toluene was evaporated in vacuo and the resulting solid was recrystallized from H$_2$O to yield 5.75 g (66%) of IVg as white plates, mp 150–3° C; IR (KBr) 3220, 2860, 1740, 1700–1660, 1385, 1300–1270, 1170 cm$^{-1}$; 1H NMR (CDCl$_3$) δ 8.73 (b s, 1H), 5.68 (s, 2H), 2.63 (s, 4H), 2.32 (s, 4H); mass spectrum, m/z (relative intensity) 165 (M , 83), 123 (32), 107 (51), 79 (100).

GENERAL PROCEDURE FOR THE N-ALKYLATION OF IMIDES OR PIPERAZINES WITH ALKYL BROMIDES.

Method D

The nitrogen-nucleophile, the alkyl bromide and potassium carbonate (K$_2$CO$_3$) were combined in CH$_3$CN and heated to reflux for 15–20 h until TLC indicated completion of reaction. The reaction was allowed to cool to ambient temperature and then filtered through a bed of Celite. The solvent was evaporated in vacuo and flash chromatography of the resultant residue yielded the desired compounds as specified below.

EXAMPLE 6

Preparation of 8-(4-Bromobutyl)-8-azaspiro[4.5]dec-2-ene-7,9-dione

The title compound was prepared from imide IVg (2.50 g, 1.00 equiv), 1,4-dibromobutane (7.4 mL, 4.09 equiv) and K$_2$CO$_3$ (4.38 g, 2.09 equiv) in 200 mL of CH$_3$CN according to the general procedure (Method D). Vacuum distillation of the resultant residue afforded the title compound (4.10 g, 90%) as a clear liquid, bp 210° C. at 0.5 mm; IR (neat) 2960, 2843, 1727, 1673, 1436, 1392, 1358, 1343, 1233, 1140 cm$^{-1}$; 1H NMR (CDCl$_3$) δ 5.66 (s, 2H), 3.80 (t, J=7.0 Hz, 2H), 3.41 (t, J=7.0 Hz, 2H), 2.68 (s, 4H), 2.27 (s, 4H), 1.94-1.58 (m, 4H); mass spectrum, m/z (relative intensity) 301 (M+2, 16), 299 (M+, 16), 220 (100), 192 (15), 178 (20).

EXAMPLE 7

8-(3-Butenyl)-8-azaspirol[4.5]decane-7,9-dione

The title compound was prepared from tetramethylene glutarimide (13.85 g, 1.00 equiv), 4-bromobutene (12.19 g, 1.09 equiv) and K$_2$CO$_3$ (13.51 g, 1.18 equiv) in 170 mL of anhydrous DMF according to the general procedure. Flash chromatography of the resultant oil in 20% EtOAc/hexane afforded the title compound (13.51 g, 75%) as a yellow oil.

EXAMPLE 8

2-Hydroxy-8-[4-[4-(1,2-benzisothiazol-1,1-dioxo-3-yl)-1piperazinyl]butyl]-8-azaspiro[4.5]decane-7,9-dione(4)

BITP sulfone 16 (1.30 g, 1.00 equiv), 2-hydroxy-8-azaspiro[-4.5]decane-7,9-dione (1.70 g, 1.03 equiv), and K (2.21 g, 3.10 equiv) were combined in 100 mL $CH_3CN$ according to Method D. Flash chromatography of the resultant residue in a 2% to 3% methanol/$CH_2Cl_2$ gradient yielded 4 (1.94 g, 77%) as a yellow solid. Recrystallization from $CH_3CN$ afforded the analytically pure test compound, m.p. 174–5° C.

EXAMPLE 9

2-Oxo-8-[4-[4-(1,2-benzisothiazol-3-yl)-1-piperazinyl]-butyl]-8-azaspiro[4.5]decane-7,9-dione(5)

This title compound was prepared from BITP 14 (6.79 g, 1.30 equiv), 2-oxo-8-(4-bromobutyl)-8-azaspiro[4.5]decane -7,9-dione (7.50 g, 1.00 equiv) and $K_2CO_3$ (10.04 g, 3.06 equiv) in 300 mL of $CH_3CN$ according to the general procedure. Flash chromatography of the resultant oil in 6% MeOH/$CH_2Cl_2$ yielded 5 (9.00 g, 83%) as an off-white foam. Conversion to the hydrochloride salt followed by recrystallization from ethanol/isopropyl ether afforded the analytically pure test compound, mp 243–5° C.

EXAMPLE 10

2-Hydroxy-8-[4-[4-(1,2-benzisothiazol-3-yl)-1-piperazinyl]butyl]-8-azaspiro[4.5]decane-7,9-dione(2)

BITP 14 (0.170 g, 1.10 equiv), 2-hydroxy-8-(4-bromobutyl)-8-azaspiro[4.5]decane-7,9-dione (0.221 g, 1.00 equiv) and $K_2CO_3$ (0.229 g, 3.10 equiv) were reacted in 30 mL of $CH_3CN$ according to the general procedure. Flash chromatography of the resultant liquid in 10% EtOH/$CHCl_3$ afforded the title compound (0.309 g, 97%) as a clear liquid. Conversion to the hydrochloride salt followed by recrystallization from $CH_3CN$/EtOAc afforded an analytically pure test compound, m.p. 223–7° C.

EXAMPLE 11

8-[4-[4-(1,2-Benzisothiazol-3-yl)-1-piperazinyl]butyl]-7,9-dioxo-8-azaspiro[4.5]decan-2-yl Decanoate (12)

8-(4-Bromobutyl)-7,9-dioxo-8-azaspiro[4.5]decan-2-yl decanoate (3.03 g, 1.00 equiv), BITP 14 (2.38 g, 1.69 equiv) and $K_2CO_3$ (3.37 g, 3.80 equiv) were reacted in 125 mL of $CH_3CN$ according to the general procedure. Flash chromatography with a 3% to 5% MeOH/$CH_2Cl_2$ gradient yielded 12 (2.02 g, 52%) as a yellow oil. Conversion to the oxalate salt and recrystallization from $CH_3CN$/EtOH afforded the analytically pure test compound, m.p. 117–9° C.

EXAMPLE 12

4-(1,2-Benzisothiazol-1,1-dioxo-3-yl)-1H-piperazine (16)

Sulfone 18 (2.8 g) was stirred into 70 mL of 1 N HCl solution and heated to 70° C. After 3 h, TLC inspection of a worked-up aliquot indicated the starting material had been consumed. The solution was allowed to cool to room temperature and then basified with 3 N NaOH solution. After repeated extractions with $CH_2Cl_2$, the combined fractions were dried over $Na_2SO_4$ and filtered. In vacuo removal of the solvent afforded the title compound as a white solid (1.31 g, 66%). Conversion to the hydrochloride salt and recrystallization from ethanol yielded the analytically pure test compound, m.p. 317–20° C.

General Procedure for the Hydroboronation-Oxidation of Cyclopentene Derivatives

Method E

To a stirring solution of the cyclopentene derivative in anhydrous THF (0.2 M solution) at 0° C. was added, over the course of 0.5 h, borane-THF complex (Aldrich; 1M solution, 1.0 equiv). The solution was stirred until TLC examination indicated total consumption of starting material (~3 h). The reaction was carefully quenched with 3N NaOH solution (0.4 equiv) followed by 30% hydrogen peroxide solution (1.2 equiv): the peroxide addition should take about 0.5 h. The reaction was stirred for 15 h and then extracted repeatedly with $CH_2Cl_2$. The combined extracts were dried on anhydrous $Na_2SO_4$, filtered and evaporated -in vacuo to afford the crude product which was purified as specified below.

EXAMPLE 13

2-Hydroxy-8-azaspiro-[4.5]decane-7,9-dione (IVh)

This compound was prepared from imide IVg according to the general procedure as a white solid in 24% yield following recrystallization from EtOAc/hexane, m.p. 131–4° C.

EXAMPLE 14

2-Hydroxy-8-(4-bromobutyl)-8-azaspiro[4.5]decane-7,9-dione

This compound was prepared from 8-(4-bromobutyl)-8-azaspiro[4.5]dec-2-ene-7,9-dione according to the procedure as a viscous liquid. Flash chromatography in EtOAc/hexane (3:2) afforded the title compound in 75% yield as a clear oil; IR (neat) 3450, 2956, 1725, 1670, 1436, 1394, 1355, 1267, 1137 $cm^{-1}$; 1H NMR ($CDCl_3$) 6 5.32 (s, 1H), 4.24 (b s, 1H), 3.81 (t, J=7.1 Hz, 2H), 3.42 (t, J=7.1 Hz, 2H), 2.82 (s, 2H), 2.61 (s, 2H), 2.09–1.53 (m, 10H); mass spectrum, m/z (relative intensity) 320 (M.H+2, 61), 318 (M+H, 68), 302 (25), 300 (25), 260 (28), 258 (28), 137 (28), 135 (30), 95 (100).

EXAMPLE 15

2-Oxo-8-(4-bromobutyl)-8-azaspiro[4.5]decane-7,9-dione

2-Hydroxy-8-(4-bromobutyl)-8-azaspiro[4.5]decane-7,9dione-(15.92 g, 1.00 equiv) was dissolved in 100 mL of $CH_2Cl_2$ and added to a solution of PCC (120 g, 11 equiv) in 500 mL of $CH_2Cl_2$ and stirred at room temperature for 2 h. The solution was filtered through a bed of celite and the salts were washed with $CH_2Cl_2$. The solvent was evaporated in vacuo to give a red-brown sludge which was flash chromatographed in 20% EtOAc/hexane to afford the title compound (15.50 g, 98%) as a clear oil.

EXAMPLE 16

8-(4-Bromobutyl)-7,9-dioxo-8-azaspiro[4.5]decan-2-yl Decanoate

2-Hydroxy-8-(4-bromobutyl)-8-azaspiro[4.5]decane-7,9dione (2.55 g, 1.00 equiv) was dissolved in 100 mL of anhydrous CH₃CN and cooled in an ice-water bath to 0° C. Decanoyl chloride (1.80 mL, 1.08 equiv) was added dropwise neat. The ice-water bath was removed and the reaction was stirred an additional 18 h. The solvent was removed in vacuo and the resultant oil was flash chromatographed with 20% EtOAc/hexane to yield the title compound (3.03 g, 80%) as a clear liquid.

EXAMPLE 17

8-[4-[4-(1,2-Benzisothiazol-3-yl)-1-piperazinyl]butyl]-6-(4-nitrobenzyloxycarboxy)--8-azaspiro[4.5]decane-7,9-dione To a solution of 8-[4-[4-(1,2-benzisothiazol-3-yl)-1piperazinyl]butyl]-8-azaspiro[-4.5]decane-7,9-dione (i) (3.00 g, 6.82 mmol) in THF (30 mL) was added a 1M solution of LiN(Me at −78° C. under Ar. The solution was stirred at −78° C. for 3 h and then a solution of di-4-nitrobenzyl peroxydicarbonate (2.94 g, 7.50 mmol) in THF (20 mL) was added over 10 min. Stirring was continued at −78° C. for 1.5 h and then acetic acid (0.43 mL, 7.5 mmol) was added. The cooling bath was removed and the reaction mixture was poured into a solution of H₂O (50 mL) and EtOAc (75 mL). The organic phase was separated and washed with H 0 (50 mL) and then the combined aqueous phases were extracted with EtOAc (75 mL). The combined organic layers were washed with brine (2×50 mL), dried (Na₂SO₄) and evaporated to give a viscous oil. Flash chromatography (EtOAc) of this oil gave the title compound (2.05 g, 47%) as a light yellow foam; IR (neat) 1760, 1735, 1630 cm⁻¹; ¹H NMR (CDCl₃) δ) 8.24 (d, J=8.8 Hz, 2H), 7.88 (dd, J=8.0, 1.1 Hz, IH), 7.78 (dd, J=8.0, 1.1 Hz, 1H), 7.57 (d, J=8.8 Hz, 2H), 7.48-7.29 (m, 2H), 5.37, 5.30 (q, J=13.4 Hz, 2H), 5.26 (s, 1H), 3.80-3.74 (m, 2H), 3.55-3.50 (m, 4H), 2.84, 2.56 (q, J=17.4 Hz, 2H), 2.66-2.61 (m, 4H), 2.45-2.38 (m, 2H), 1.8-1.3 (b m, 12H).

EXAMPLE 18

8-[4-[4-(1,2-Benzisothiazol-3-yl)-1-piperazinyl]butyl]-6-hydroxy-8-azaspiro[-4.5]decane-7,9-dione (10)

A mixture of 8-[4-[4-(1,2-benzisothiazol-3-yl)-1piperazinyl]butyl]-6-(4-nitro-benzyloxycarboxy)-8-azaspiro [4.5]decane-7,9-dione (1.98 g, 3.12 mmol) and 10% Pd/C (0.75 g) in MeOH-THF (2:1, 30 mL) was hydrogenated in a Parr shaker at 55 psi for 1.5 h. An additional 1.25 g of 10% Pd/C was added and hydrogenation was continued at 55 psi for 1 h. The resulting mixture was filtered through a pad of Celite and the pad was washed with EtOAc. The filtrate was evaporated to give a gum which was purified by flash chromatography (EtOAc) to give the title compound (0.98 g, 69%) as a solid. An analytical sample was crystallized from EtOAc/hexane to give pale yellow crystals, m.p. 151° C.; IR (neat) 3430, 1728, 1673 cm⁻¹; 1H NMR (CDCl₃) δ 7.90-7.76 (m, 2H), 7.49-7.29 (m, 2H), 4.18 (s, 1H), 3.82-3.69 (m, 2H), 3.59-3.54 (m, 5H), 2.79, 2.52 (AB q, J=17.4 Hz, 2H), 2.75-2.66 (m, 4H), 2.49-2.44 (m, 2H), 2.11-1.98 (m, 1H), 1.74-1.19 (b m, llH);
Anal. calcd for C₂₄H₃₂N₄O₃S:
C, 63.13; H, 7.06; N, 12.27.
Found: C, 62.76; H, 7.10; N, 12.06.

EXAMPLE 19

6-[N-[4-[4-(1,2-Benzisothiazol-3-yl)-1-piperazinyl]butyl]carbamoyl]-7-oxaspiro[4.4]-nonane-8-one (13)

A mixture of 8-[4-[4-(1,2-benzisothiazol-3 yl)-1piperazinyl]butyl]-6-hydroxy-8-azaspiro[4.5]decane-7,9dione (1.14 g, 2.5 mmol) and KF-Al₂O₃ (0.36 g, ~1 equiv) in acetonitrile (25 mL) was vigorously stirred at room temperature under Ar for 4 h. The supernatant was then decanted and replaced with fresh acetonitrile (25 mL), and stirring was continued for 4 h. This process was repeated until the residue contained no more starting material (5× in total). The combined supernatants were evaporated and the resulting gum was purified by flash chromatography (EtOAc, then EtOAc acetone (1:1) to give the title compound (0.75 g, 66%) as an off-white foam. A 650 mg sample of the title compound was dissolved in excess ethanolic HCl and the solution was evaporated to dryness. The residue was taken up in acetone, ether was added and the resulting solid was collected and dried in vacuo to give 620 mg of a cream-colored powder, m.p. 194-197° C. An analytical sample was prepared by trituration with acetone to give the hydrochloride as a white powder; IR (CH₂Cl₂) 3430, 1785, 1680 cm⁻¹; 1H NMR (CDCl₃) δ 7.86-7.80 (m, 2H), 7.54-7.36 (m, 2H), 7.29 (b s, 1H), 4.77 (s, 1H), 4.12-4.08 (m, 4H), 3.56-3.50 (m, 2H), 3.47-3.33 (m, 2H), 3.14-3.04 (m, 4H), 2.62, 2.37 (q, J=17.1 Hz, 2H), 2.1-1.4 (b m, 13H); Anal. calcd for C₂₄H₃₂N₄O₃S/1.4 HCl:
C, 56.78; H, 6.63; N, 11.04.
Found: C, 56.84; H, 6.73; N, 11.20.

EXAMPLE 20

8-(3,4-Epoxybutyl)-8-azaspiro[4.5]decane-7,9-dione

A solution of MCPBA (80%, 5.01 g, 1.13 equiv) in 50 mL of CH₂Cl₂ was added to a stirring solution of 8-(3-butenyl) -8-azaspiro[4.5]decane-7,9-dione (4.54 g, 1.00 equiv) in 0 mL of CH₂Cl₂. The resulting solution was stirred until TLC inspection indicated the absence of limiting reagent (δ15 h). The reaction was quenched with 40 mL of 2% Na₂CO₃ solution and transferred to a separatory funnel. The layers were separated and the organic phase was washed with 2% Na solution (3×20 mL). The combined aqueous layers were back-extracted with CH₂Cl₂ (40 mL). The combined organic layers were dried on anhydrous Na₂SO₄, filtered and the solvent removed in vacuo. Flash chromatography of the resulting residue in 25% EtOAc/hexane afforded the title compound (3.65 g, 75%) as a clear, viscous liquid.

EXAMPLE 21

8-[4-[4-(1,2-Benzisothiazol-1-oxo-3-yl)-1-piperazinyl]-3hydroxybutyl]-8-azaspiro[4.5]decane-7,9-dione (8)

8-(3,4-Epoxybutyl)-8-azaspiro[4.5]decane-7,9-dione (2.43 g, 1.00 equiv), BITP sulfoxide 15 (3.10 g, 1.28 equiv) and K₂CO₃ (2.85 g, 1.01 equiv) were combined in 100 mL of CH₃CN and refluxed until TLC inspection indicated complete consumption of the limiting reasent (δ20 h). The reaction was allowed to cool to room temperature and then filtered through a bed of Celite. The solvent was stripped in vacuo and the resulting oil was flash chromatographed in a 3% to 5% MeOH/CH₂Cl₂ gradient to yield 8 (2.48 g, 51%) as a yellow foam. Conversion to the hydrochloride salt followed by recrystallization from CH₃CN/EtOH afforded the analytically pure test compound, m.p. 235° C. 1,1-Dimethylethyl 4-(1,2-Benzisothiazol-1,1-dioxo-3-yl)-2-oxo-1-piperazinecarboxylate Formula I, II and III. Table 7 contains in vivo biological data for representative compounds of Formula I, II and III.

TABLE 3

Selected Formula I Compounds

| Reference # | $R^1$ | $R^2$ | $R^3$ | $R^4$ | X | Analyzed Formula | mp(°C.) |
|---|---|---|---|---|---|---|---|
| 1 | H | H | H | H | $SO_2$ | $C_{24}H_{32}N_4O_4S$ | 185–7 |
| 2 | HO | H | H | H | S | $C_{24}H_{32}N_4O_3S/HCl$ | 223–7 |
| 3 | HO | H | H | H | SO | $C_{24}H_{32}N_4O_4S/C_4H_4O_4$ | 92–4 |
| 4 | HO | H | H | H | $SO_2$ | $C_{24}H_{32}N_4O_5S$ | 174–5 |
| 5 | O | H | H | H | S | $C_{24}H_{30}N_4O_3S/HCl$ | 243–5 |
| 6 | O | H | H | H | SO | $C_{24}H_{30}N_4O_4S/HCl/0.2H_2O$ | 203–6 |
| 7 | H | H | HO | H | S | $C_{24}H_{32}N_4O_3S/HCl$ | 212–4 |
| 8 | H | H | HO | H | SO | $C_{24}H_{32}N_4O_4S/HCl/0.25H_2O$ | 235 |
| 9 | HO | H | HO | H | S | $C_{24}H_{32}N_4O_4S/HCl/0.2H_2O$ | 167–9 |
| 10 | H | HO | H | H | S | $C_{24}H_{32}N_4O_3S$ | 151 |
| 11 | H | HO | H | H | SO | $C_{24}H_{32}N_4O_4S$ | 171–2 |
| 12 | $C_9H_{19}CO_2$ | H | H | H | S | $C_{34}H_{50}N_4O_4S/C_2H_2O_4$ | 117–9 |

Ruthenium dioxide hydrate (60%, 0.3206 g, 0.35 equiv) was added to a solution of $NaIO_4$ (8.92 g, 10.2 equiv) in 75 mL of $H_2O$. The clear solution immediately took on the color and consistency of bright yellow milk. 1,1-Dimethylethyl 4-(1,2-benzisothiazol-3-yl)-1-piperazinecarboxylate (1.31 g, 1.00 equiv) was slowly added via addition funnel as a solution in 90 mL of $CH_2Cl_2$. The biphasic solution proceeds from yellow to dark green to black in minutes. The solution was vigorously stirred for 20 h after which the phases were separated and the aqueous layer was twice extracted with $CH_2Cl_2$. The combined organic fractions were filtered through a bed of Celite, dried over anhydrous $Na_2SO_4$, filtered and evaporated in vacuo to a blackish solid. Flash chromatography in an EtOAc/hexane (1:1) to EtOAc gradient afforded the title compound (890 mg, 65%) as a white solid, m.p. 128–30° C.; IR (KBr) 1778, 1735 cm$^{-1}$; 1H NMR (CDCl$_3$) δ 7.90 (m, 2H), 7.71 (m, 2H), 4.70 (b s, 2H), 4.15 (b m, 4H), 1.37 (s, 9H); mass spectrum, m/z (relative intensity) 266 (100).

EXAMPLE 23

4-(1,2-Benzisothiazol-1,1-dioxo-3-yl)-2-oxo-1H-piperazine (17)

1,1-Dimethylethyl 4-(1,2-benzisothiazol-1,1-dioxo-3-yl)-2-oxo-1-piperazinecarboxylate (800 mg) was heated in a flask to 200° C. The white solid was observed to rapidly melt and evolve gas. When the bubbling ceased, the flask was allowed to cool and the resultant solid was flash chromatographed in a 3% to 7.5% MeOH/$CH_2Cl_2$ gradient to give the title compound (575 mg, 99%) as an off-white solid, m.p. >250° C.

By appropriate modification of the reaction sequences shown in Schemes I-VI and the various synthetic reactions exemplified above, the instant compounds of Formulas I, II and III may be synthesized. The reference number, substitution pattern and physical data for selected Formula I, II and III compounds can be found in Tables 3, 4 and 5, respectively. Table 6 contains in vitro binding data for representative compounds of

TABLE 4

Selected Formula II Compounds

| Reference # | X | Analyzed Formula | mp(°C.) |
|---|---|---|---|
| 13 | S | $C_{24}H_{31}N_4O_3S/1.4HCl$ | 194–7 |

TABLE 5

Selected Formula III Compounds

| Reference # | Z | $R^4$ | X | Analyzed Formula | mp (°C.) |
|---|---|---|---|---|---|
| 14 | H | H | S | $C_{11}H_{13}N_3S/HCl$ | 283–6 |
| 15 | H | H | SO | $C_{11}H_{13}N_3SO$ | 262–4 |
| 16 | H | H | $SO_2$ | $C_{11}H_{13}N_3O_2S/HCl/0.25H_2O$ | 317–20 |
| 17 | H | O | $SO_2$ | $C_{11}H_{11}N_3SO_3$ | >250 |
| 18 | tBoc | H | $SO_2$ | $C_{16}H_{21}N_3O_4S$ | 192–4 |
| 19 | $EtO_2C$ | H | $SO_2$ | $C_{14}H_{17}N_3O_4S$ | 192–6 |

TABLE 6

| Reference # | Representative In Vitro Receptor Binding (RB) Data [IC$_{50}$ (nM)] | | | |
|---|---|---|---|---|
| | RB1 | RB2 | RB3 | RB4 |
| i | 8.4 | 47 | 0.40 | 2.85 |
| ii | 3490 | 331 | 276 | 1120 |
| 1 | >1000 | 274 | 25,000 | |
| 2 | 52.5 | 0.876 | 2.05 | 3.75 |
| 3 | >100,000 | 372 | 1480 | 1850 |
| 5 | 68.3 | 1.30 | 2.92 | 2.99 |
| 7 | 111 | 8.30 | 10.2 | 24.9 |
| 9 | 491 | 7.15 | 19.8 | 14.2 |
| 10 | 39.2 | 1.63 | 1.10 | 5.06 |
| 12 | 153 | 7.22 | 10.2 | 35.8 |
| 14 | >1000 | 510 | 110 | 179 |
| 17 | — | 13,100 | >100,000 | >1000 |
| 18 | >1000 | >100,000 | — | >100,000 |

TABLE 7

| Reference # | Representative In Vivo Biological Data | |
|---|---|---|
| | CAR ED$_{50}$ (mg/kg) | APO ED$_{50}$ (mg/kg) |
| i | 10.9 p.o. | 13.1 p.o. |
| ii | 7.6 p.o. | 9.6 p.o. |
| 1 | >100 p.o. | >100 p.o. |
| 2 | >100 p.o. | — |
| 5 | 60.3 s.c. | >50 s.c. |
| 7 | >80 p.o. | — |
| 10 | 8.4 p.o. | 26 p.o. |

What is claimed is:

1. A compound of Formula I

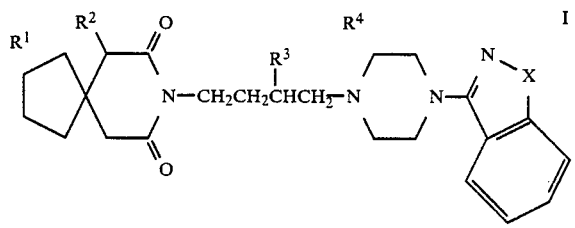

wherein $R^1$ is selected from the gorup consisting of hydrogen, hydroxyl, lower ($C_1$–$C_4$) alkoxy, higher ($C_9$–$C_{17}$) acyloxy, and oxo;

$R^2$ is selected from hydrogen, methyl, hydroxyl, lower ($C_1$–$C_4$) alkoxy, higher ($C_9$–$C_{17}$) acyloxy, and acetoxy;

$R^3$ is hydrogen, hydroxyl, and methoxy;

$R^4$ is hydrogen or oxo, with the proviso that $R^1$ and $R^2$ cannot be acyloxy simultaneously and further $R^1$, $R^2$, $R^3$, and $R^4$ cannot be hydrogen simultaneously; the solid and dotted lines refer to either a double covalent bond or a single covalent bond with another hydrogen atom covalently bonded to the carbon terminus end; and X is S or SO, or a pharmaceutically acceptable salt or solvate thereof.

2. A compound of Formula II

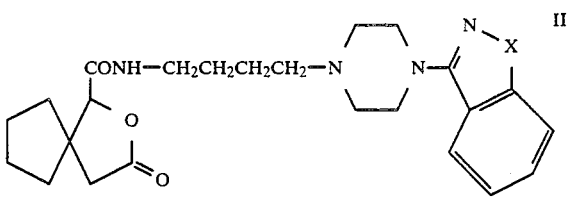

wherein X is selected from the gorup consisting of S, SO, and SO$_2$; or a pharmaceutically acceptable acid addition salt and solvate thereof.

3. The compound of claim 1, wherein said compound is 8-[4-[4-(1,2-benzisothiazol-3-yl)-1-piperazinyl]butyl]-2-hydroxy-8-azaspiro[4.5]decane-7,9-dione.

4. The compound of claim 1, wherein said compound is 8-[4-[4-(1-oxo-1,2-benzisothiazol-3-yl)-1-piperazinyl]butyl]-2-hydroxy-8-azaspiro[4.5]decane-7,9-dione.

5. The compound of claim 1, wherein said compound is 8-[4-[4-(1,2-benzisothiazol-3-yl)-1-piperazinyl]butyl]-2-oxo-8-azaspiro[4.5]-decane-7,9-dione.

6. The compound of claim 1, wherein said compound is 8-[4-[4-(1-oxo-1,2-benzisothiazol-3-yl)-1-piperazinyl]butyl]-2-oxo-8-azaspiro-[4.5]decane-7,9-dione.

7. The compound of claim 1, wherein said compound is 8-[4-[4-(1,2-benzisothiazol-3-yl)-1-piperazinyl]butyl]-6-hydroxy-8-azaspiro[-4.5]decane-7,9-dione.

8. The compound of claim 1, wherein said compound is 8-[4-[4-(1,2-benzisothiazol-1-oxo-3-yl)-1-piperazinyl-]butyl]-6-hydroxy-8-azaspiro[4.5]decane-7,9-dione.

9. The compound of claim 1, wherein said compound is 8-[4-[4-(1,2-benzisothiazol-3-yl)-1-piperazinyl]-3hydroxybutyl]-8-azaspiro[-4.5]decane-7,9-dione.

10. The compound of claim 1, wherein said compound is 8-[4-[4-(1,2-benzisothiazol-1-oxo-3-yl)-1-piperazinyl]-3-hydroxybutyl]-8-azaspiro[4.5]decane-7,9-dione.

11. The compound of claim 1, wherein said compound is 8-[4-[4-(1,2-benzisothiazol-3-yl)-1-piperazinyl]-3hydroxybutyl]-2-hydroxy-8-azaspiro[4.5]decane-7,9dione.

12. The compound of claim 1, wherein said compound is 8-[4-[4-(1,1-dioxo-1,2-benzisothiazol-3-yl)-1-piperazinyl]butyl]-2-hydroxy-8-azaspiro[4.5]decane-7,9-dione.

13. The compound 4-(1,2-benzisothiazol-1,1-dioxo-3yl)-2oxo-1H-piperazine of the formula

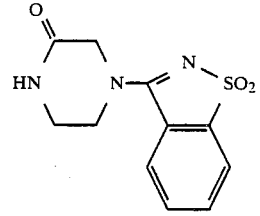

14. The compound 1,1-dimethylethyl 4-(1,1-dioxo-1,2-benzisothiazol-3-yl)-1-piperazinecarboxylate pf the formula 15. The compound ethyl 4-(1,1-dioxo-1,2-benzisothiazol3yl)-1-piperazinecarboxylate pf the formula

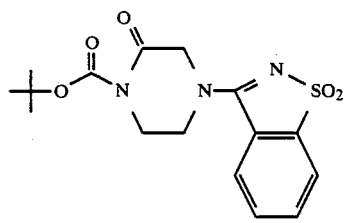

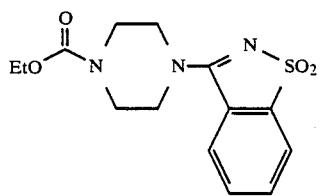

16. The compound of claim 1, wherein said compound is 8-[4-[4-(1,2-benzisothiazol-3-yl)-3-piperazinyl]-butyl]-7,9-dioxo-8-azaspiro[4.5]decan-2-yl decanoate.

17. The compound of claim 2, wherein said compound is 6-[N[4-[4-(1,2-benzisothiazol-3-yl)-1-piperazinyl) butyl]carbamoyl]-7-oxaspiro[4.4]nonane-8-one.

18. A process for ameliorating a psychotic state in a mammal in need of such treatment which comproses systemic administration to said mammal of an effective antipsychotic dose of a compound of claim 1.

19. A process for ameliorating a psychotic state in a mammal in need of such treatmetn which comprises systemic administration to said mammal of an effective antipsychotic dose of a compound of claim 2.

20. A pharmaceutical composition comprising an effective antipsychotic amount of a compound of claim 1 and a pharmaceutically acceptable carrier.

21. A pharmaceutical composition comprising an effective antipsychotic amount of a compound of claim 2 and a pharmaceutically acceptable carrier.

* * * * *

UNITED STATES PATENT AND TRADEMARK OFFICE
CERTIFICATE OF CORRECTION

PATENT NO. : 4,956,368

DATED : Sep. 11, 1990

INVENTOR(S) : Joseph A. Cipollina, Middletown, Conn.
Edward H. Ruediger, Greenfield Park, Canada It is certified that error appears in the above-identified patent and that said Letters Patent is hereby corrected as shown below:

Throughout the specification, formulas which should have the moieties $-R^1\equiv-$ and $-R^4\equiv-$ were erroneously printed as "$R^1=$" and "$R^4=$", respectively. Such errors appear at:

- Formula I, in the Abstract, page 1;
- Formula I, column 1, lines 30-38;
- Formula III, column 3, lines 40-50;
- Formula I, column 4, lines 26-35;
- Formula III, column 5, lines 1-10;
- Formulas Ia and Ib, column 7, lines 43-64;
- Formulas IIa and IIIa, column 8, lines 3-21;
- Formulas IIIb, and IIIc, column 9, lines 3-21;
- Formulas Va and Vb, column 11, lines 6-37;
- Formula I, column 22, in Table 3; and
- Formula III, column 22, in Table 5.

Column 3, line 44, in Formula III, "N" should read --X--.
Column 5, line 5, in Formula III, "N" should read --X--.

UNITED STATES PATENT AND TRADEMARK OFFICE
CERTIFICATE OF CORRECTION

PATENT NO. : 4,956,368

DATED : Sep. 11, 1990

INVENTOR(S) : Joseph A. Cipollina, Middletown, Conn.
Edward H. Ruediger, Greenfield Park, Canada It is certified that error appears in the above-identified patent and that said Letters Patent is hereby corrected as shown below:

In Claim 1, the radicals $R^1$ and $R^4$ of Formula I were drawn with no bonds. Rather, Formula I should appear as:

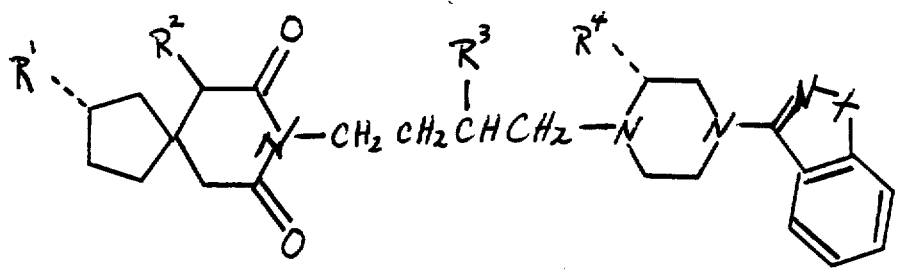

In Claim 1, line 49 delete "gorup" and substitute with -group-.

In Claim 2, line 11, delete "gorup" and substitute with -group-.

In Claim 9, line 36, delete "8-[4-[4-(1,2-benzisothiazol-3-yl)-1-piperazinyl]-3hy-" and substitute with - 8-[4-(4-(1,2-benzisothiazol-3-yl)-1-piperazinyl]-3-hy- -.

In Claim 11, line 46, delete "3hydroxybutyl]-2-hydroxy-8-azaspiro[4.5]-decane-" and substitute with - 3-hydroxybutyl]-2-hydroxy-8-azaspiro[4.5]-decane -.

UNITED STATES PATENT AND TRADEMARK OFFICE
CERTIFICATE OF CORRECTION

PATENT NO. : 4,956,368

DATED : Sep. 11, 1990

INVENTOR(S) : Joseph A. Cipollina, Middletown, Conn.
Edward H. Ruediger, Greenfield Park, Canada It is certified that error appears in the above-identified patent and that said Letters Patent is hereby corrected as shown below:

In Claim 13, line 54, delete "3yl-2oxo-1H-piperazine" and substitute with - 3-yl-2:oxo-1H-piperazine -.

In Claim 14, line 67, delete "pf" and substitute with -of-.

In Claim 15, delete space between lines 25-31.

In Claim 15, line 31, delete "thiazol3yl)-1-piperazinecarboxylate pf" and substitute with - thiazol-3-yl)-1-piperazinecarboxylate of -.

In Claim 19, line 22, delete "treatmetn" and substitute with -treatment-.

Signed and Sealed this

Twenty-first Day of January, 1992

Attest:

HARRY F. MANBECK, JR.

*Attesting Officer*        Commissioner of Patents and Trademarks